United States Patent
Ishibashi et al.

(10) Patent No.: US 6,843,981 B1
(45) Date of Patent: Jan. 18, 2005

(54) TOOTH BLEACHING COMPOSITIONS AND METHODS OF BLEACHING DISCOLORED TOOTH

(75) Inventors: Takuro Ishibashi, Nagasaki (JP); Emi Higashiizumi, Ibaraki (JP); Ryuji Sotoaka, Ibaraki (JP); Fukusaburo Ishihara, Ibaraki (JP); Minoru Kakuda, Ibaraki (JP); Masumi Ogasawara, Ibaraki (JP); Kouzo Ishibashi, Nagasaki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/019,408

(22) PCT Filed: Jul. 3, 2000

(86) PCT No.: PCT/JP00/04397

§ 371 (c)(1),
(2), (4) Date: Dec. 28, 2001

(87) PCT Pub. No.: WO01/01943

PCT Pub. Date: Nov. 1, 2001

(30) Foreign Application Priority Data

Jul. 2, 1999 (JP) .......................................... 11/188858

(51) Int. Cl.$^7$ ............................. A61K 7/16; A61K 7/20; A61C 5/00
(52) U.S. Cl. ........................... 424/53; 433/80; 433/215; 433/216; 433/229
(58) Field of Search .............................. 424/53; 433/80, 433/215, 216, 229; 514/770, 949

(56) References Cited

U.S. PATENT DOCUMENTS

| | | | |
|---|---|---|---|
| 4,603,045 A | * 7/1986 | Smigel | 424/53 |
| 4,690,776 A | * 9/1987 | Smigel | 424/53 |
| 5,032,178 A | 7/1991 | Cornell | |
| 5,041,280 A | * 8/1991 | Smigel | 424/53 |
| 5,302,374 A | * 4/1994 | Wagner | 424/53 |
| 5,597,554 A | * 1/1997 | Wagner | 424/53 |
| 5,698,205 A | * 12/1997 | Bruckner et al. | 424/401 |
| 5,759,251 A | * 6/1998 | Nakamara et al. | 106/286.4 |
| 5,902,568 A | 5/1999 | Ryles et al. | |
| 6,210,163 B1 | * 4/2001 | Cohen | 433/217.1 |
| 6,231,343 B1 | * 5/2001 | Ishibashi et al. | 433/215 |
| 6,319,513 B1 | * 11/2001 | Dobrozsi | 424/434 |
| 6,420,437 B1 | * 7/2002 | Mori et al. | 516/90 |
| 2002/0177091 A1 | * 11/2002 | Eguchi et al. | 433/29 |

FOREIGN PATENT DOCUMENTS

| | | |
|---|---|---|
| JP | 51-59097 | 5/1976 |
| WO | 99/15143 | * 4/1999 |

OTHER PUBLICATIONS

Australian Official Action dated Apr. 28, 2003, for Australian Application No. 55724/00.
Patent Abstracts of Japan, Pub. No. 11092351A (Apr. 6, 1999).
Patent Abstracts of Japan, Pub. No. 60075413A (Apr. 27, 1985).

* cited by examiner

Primary Examiner—Frederick Krass
(74) Attorney, Agent, or Firm—Antonelli, Terry, Stout & Kraus, LLP

(57) ABSTRACT

The bleaching compositions of discolored teeth comprise titanium dioxide initiating photocatalyst action with light irradiation, chemical compounds generating hydrogen peroxide in an aqueous solution and thickening agents. Further the bleaching methods of discolored teeth comprising applying the bleaching composition onto the surface area of the teeth and then initiating photocatalyst action by irradiating the applied surfaces area with light. Therefore, the present invention shows remarkable bleaching results due to easy application of the compositions onto discolored teeth and keeping the original activity of the photocatalyst without its deterioration.

19 Claims, No Drawings

US 6,843,981 B1

TOOTH BLEACHING COMPOSITIONS AND METHODS OF BLEACHING DISCOLORED TOOTH

This application is a 371 of PCT/JP00/04397, filed Jul. 3, 2000.

TECHNICAL FIELD

The present invention relates to methods for bleaching and removing colored sediment on teeth by photocatalytic action, and tooth bleaching compositions for the methods. More particularly, the present invention relates to methods for bleaching the discolored teeth by applying the bleaching composition, comprising certain compounds having photocatalytic activity, onto the discolored teeth and then irradiating the applied area with light, and also the present invention relates to the bleaching compositions for the bleaching methods.

BACKGROUND ART

Recent year, there have been increasing demand for esthetic improvements of teeth such as improvements of contours, alignment and integrity of teeth in dental therapy. In particular, there have been more cases of young women desiring such dental therapy so as to whitening teeth as an important element of beauty. Generally, the cause of dental discoloration and pigmentation or stain falls into the two categories: (1) extrinsic causes such as sedimentation of colored materials (tobacco, tea, etc.), pigment generating bacteria, discoloration of filling materials (primarily composite resins) and metal salts (primarily amalgam, silver nitrite, and ammonia silver); and (2) intrinsic causes such as aging, chemicals or medicine (ex. fluorine and tetracyclines), dysmmetabolism and hereditary, and dental injuries. The National Health Insurance is applicable to bleaching methods for, the latter, discolored teeth intrinsically.

Several methods have been proposed as methods for esthetic improvement of discolored teeth, among which bleaching may be considered as a highly effective method for the preservation of dentine if a suitable method for each decease case would be selected and carried out properly, although there may be some cases of color reversion. Bleaching is basically a method for decolorizing colored materials through a chemical reaction. In the past, there were various reports of bleaching agents comprising a variety of chemicals based on vital bleaching and non-vital bleaching as well as bleaching methods using such agents.

The following are typical examples:

(1) Bleaching method using 30% $H_2O_2$ as a chemical combining light and heat in parallel.

This is a method in which strips of gauze soaked in 30% $H_2O_2$ are placed on the front surfaces of teeth and are irradiated for 30 minutes from the left and right by using two 500 W photographic lamps. In this method, the lamps are set as close to the gauze as possible and the $H_2O_2$ should be replenished about every 5 minutes so as to prevent them from drying.

(2) Bleaching method using 30% $H_2O_2$ as a chemical combining high frequency current in parallel.

This is a method in which strips of gauze soaked in 30% $H_2O_2$ are placed on the front surface of teeth and high frequency current is delivered for one second with a spoon-shaped tip of a frequency scalpel and is not delivered for 8 second. The operation should be repeated 6 to 8 times and $H_2O_2$ should be replenished to keep them wet during the treatment.

(3) Bleaching method using a paste comprising Aerosol (fine silica powder) mixed with 35% $H_2O_2$ and the paste is applied.

This is a method in which the paste is applied onto the surfaces of the etched teeth, 15 minutes later the teeth are rinsed with water and then polished. The method gives a highly bleaching result without using light or heat as Aerosol serves as a moisturizing material to prevent the bleaching agent from drying out and also enhances the bleaching effects. The 35% $H_2O_2$ should be handled with care due to its highly corrosive property.

(4) Bleaching method using a paste (Shofu Hi-Lite:tradename), obtained by kneading a 35% $H_2O_2$ solution and a powder comprising potassium sulfate, manganese sulfate, silicon dioxide or the like, as a chemical.

This is a method in which the paste is placed on the front surfaces of teeth and worked for 10 minutes or irradiated it with light for 3 minutes by applying a visible light ray radiation device. An advantage of the method is as follows: The paste shows a light green immediately after the kneading and then turn yellow by the light irradiation. If the paste turns dark-brown immediately after the kneading, this indicates that the bleaching effects of the liquid have diminished. However there is the same disadvantage mentioned the above due to the use of 35% $H_2O_2$.

(5) Bleaching method using a mixture of 1 ml of 30% HCl, 1 ml of 30% $H_2O_2$, and 0.2 ml of diethyl ether as chemical (Improved Machines bleaching).

In this method, the mixture is allowed to act for 5 minutes on tooth surfaces, and then the teeth are polished for 15 minutes under light pressure using a polishing disc. The treatment is repeated 3 times, then they are neutralized with 5.25% NaOCl and the teeth are thoroughly rinsed with water (Oral Surg., 26: 871–878(1968), J. Am. Dent. Assoc., 87: 1329(1973)). In this method, since the paste may scatter into the patient's eyes, it is necessary to protect them from it adequately.

(6) Bleaching method using a paste obtained from kneading 30% $H_2O_2$ and a sodium perborate powder (Walking bleach method).

In this method, to dilate the dentinal canaliculus and enhance the bleaching effects, the walls in the pulp cavity are treated with phosphoric acid for 1 minute, rinsed with water and dried. Then the paste is introduced into the pulp cavity and temporarily sealed with cement. Although this method is currently, widely applied for clinical purposes to which the National Health Insurance is applicable as a simple and highly effective method. Its disadvantage is the same as that mentioned in (3).

There have been other many bleaching methods reported as follows: The dental bleaching method using the bleaching agent comprising a mixture of aqueous hydrogen peroxide and ortho-phosphoric acid (Japanese Patent Application Laid-Open No. H8-143436/1996). The bleaching agent obtained from mixing silicic acid anhydride with aqueous hydrogen peroxide and the vital bleaching method using the bleaching agent (Japanese Patent Application Laid-Open No. H5-320033/1993). Further, the dental bleaching compositions comprising a dental bleaching agent (hydrogen-urea peroxide, hydrogen peroxide-carbamide, carbamide peroxide, and the like) and a matrix such as carboxymethylen, and a bleaching method using such a dental bleaching agent (Japanese Patent Application Laid-Open No. H8-113520/1996).

On the other hand, bleaching methods and bleaching agents for dental bleaching require the following conditions:
(a) pronounced bleaching results,
(b) none toxicity of bleaching agents
(c) easy operations,
(d) no detraction to dental physical properties after bleaching,
(e) efficacious for vital tooth bleaching as well as non-vital tooth bleaching,
(f) speedy bleaching results, and so on.

A bleaching method fulfilling the above conditions would be capable of affording aesthetic improvement while keeping dental contour with remarkably improved results. However, in conventional bleaching agents or methods, the primary bleaching agent is 30% to 35% aqueous hydrogen peroxide, which is highly corrosive and its oxidative property is the base for bleaching teeth. Anyhow, all of various bleaching methods carried out currently in Japan should be the combination of 30% to 35% aqueous hydrogen peroxide, various utensils and other chemicals. A bleaching method carried out in U.S.A. has been the use of 10% urea peroxide in lieu of 30% to 35% aqueous hydrogen peroxide, however, this method has been litigated over the problems in terms of efficacy and safety, and has not obtained the governmental approval in Japan.

Taking the aforementioned status of the bleaching methods into the consideration, the inventors of the present invention have found that, without using highly toxic 30% to 35% aqueous hydrogen peroxide, the intended objectives were achieved by the combined use of titanium dioxide having photocatalytic action and low concentration aqueous solution of hydrogen peroxide as efficacious constituents. The bleaching method using the combination shows safer and simpler, and also is remarkably efficacious to vital tooth as well as non-vital tooth (Japanese Patent Application Laid-Open No. H11-92351/1999).

DISCLOSURE OF THE INVENTION

However, the aforementioned methods have the following disadvantages: it is very difficult to apply the surfaces of teeth with enough amounts of bleaching agent, that causes to unsatisfied bleaching results. Therefore, it is necessary to prepare a paste type of a bleaching agent by increasing the content of titanium dioxide so as to make the application easier. The increased content of it interferes the photocatalytic action because titanium dioxide is non-transparent against irradiation light.

It is the objectives of the present invention to provide the bleaching compositions and also the bleaching methods. The compositions and methods overcome the problems mentioned above, are easily applied on discolored teeth in practice, thereby obtain sufficient bleaching results without any deterioration of the photocatalytic activity, and have superior safety.

So as to solve the above problems, the present invention is composed of the following technical means:
(1) Tooth bleaching composition characterized by containing titanium dioxide initiating a photocatalytic action by irradiation of light, a chemical compound generating hydrogen peroxide in an aqueous solution and a thickening agent,
(2) Tooth bleaching composition according to above (1) wherein titanium dioxide is anatase-type, rutile-type or brookite-type,
(3) Tooth bleaching composition according to above (1) or (2), wherein the chemical compound is selected from the group consisting of hydrogen peroxide, perborate, percarbonate, persulfate, perphosphate, calcium peroxide, magnesium peroxide and urea peroxide,
(4) Tooth bleaching composition according to any one of above (1) to (3), wherein the thickening agent is layer-structure clay minerals, phosphoric acid or phosphate,
(5) Tooth bleaching composition according to above (4), wherein the thickening agent is an inorganic clay mineral selected from the group consisting of saponite, montmorillonite, stevensite, hectonite, smecnite, nacrite and sepiolite,
(6) Tooth bleaching composition according to above (4), wherein phosphate is tetra-sodium pyrophosphate,
7) (7) Tooth bleaching composition according to any one of above (1) to (6), wherein the content of the chemical compound generating hydrogen peroxide in an aqueous solution is 35% by weight or less.
(8) Methods for bleaching discolored teeth by applying the tooth bleaching composition onto the surfaces of the discolored teeth and then irradiating the applied surface area with light, and
(9) Methods according to above (8), wherein the wavelength of the irradiating light is 300 nm or longer.

PREFERRED EMBODIMENT OF THE INVENTION

So as to achieve the objectives mentioned above, the present invention utilizes titanium dioxide initiating photocatalytic action by light irradiation and tooth bleaching compositions containing a thickening agent, thereby remarkable results of discolored teeth bleaching as well as improved application ability during treatment are brought in. In the present invention, it is defined that the term of discoloration has broad meanings including pigmentation and stain.

In preferred embodiments, the tooth bleaching compositions of the present invention are composed of solution or paste comprising titanium dioxide, a chemical compound generating hydrogen peroxide in aqueous solution and a thickening agent. Although any types of titanium dioxide, without regard to its form or property, is possible to use for the invention only if it initiates the photocatalytic action, the anatase-type, the rutile-type and the brookite-type are preferred. Further, the titanium oxide improved its affinity to a tooth surface by coating the surface of the titanium dioxide with calcium phosphate is probable to use. Furthermore, the titanium dioxide of which photocatalytic activity is improved by depositing platinum on it or the titanium dioxide treated by plasma and the like which initiate the photocatalytic action by visible light is probable to use. Titanium dioxides of powder-type or sol-type obtained from dispersing it into a medium such as water can be employed too. The titanium dioxide of the particle diameter 1 to 500 nm is suitable for the use, further the particle diameter 5 to 200 nm is preferable to it. A small amount of the titanium dioxide content effects reasonably, however, a very small amount of the titanium dioxide content takes longer time so as to obtain reasonable results which depends on the intensity of tooth discoloration. On the other hand, too high content of it inversely causes lowering the bleaching effects due to titanium dioxide's low light penetration. Therefore, the preferred content of titanium dioxide in the bleaching compositions is 0.001 to 10% by weight. The content of 0.01 to 1% by weight is more preferable, and the content of 0.01 to 0.1% by weight is further more preferable.

Any chemical compound, if it generates hydrogen peroxide by making its aqueous solution, is to be used for the present invention. The chemical compounds generating hydrogen peroxide in a aqueous solution suitable for the present invention is, for example, hydrogen peroxide, perborate, percarbonate, persulfate, perphosphate, calcium peroxide, magnesium peroxide, urea peroxide, and the like. Hydrogen peroxide is preferable. The very small amount of the chemical compounds generating hydrogen peroxide mentioned above are able to show remarkable bleaching results by comparing with conventional bleaching compounds. Therefore, the content of the chemical compound in the bleaching compositions is preferably 35% by weight or less, more preferably 10% by weight or less and further more preferably 5 to 10% by weight. If the content is higher than the maximum range, there is no much difference in the bleaching results but it has disadvantage in view of safety.

Aqueous type of the thickening agents is preferred for the thickening agents being used for the present invention. Aqueous organic polymer, aqueous emulsion, clay minerals, phosphate and, the like are the examples of the aqueous type of the thickening agents. In case of the aqueous type of the thickening agent comprising an organic compound as its main constituent, active oxygen generated by photocatalyst action of titanium dioxide is not only used for the tooth bleaching but also consumed for the reaction with the thickening agents. Therefore, it is preferred to use clay minerals and inorganic compounds such as phosphoric acid, phosphate and so on in the present invention. It is furthermore preferred to use layer-structure inorganic clay minerals, phosphoric acid or phosphate.

Inorganic clay minerals are generally, roughly classified into a fibrous structure type (ex. sepiolite, attapulgite, etc), a non-crystal structure type (ex. allophane, etc), mixed layer structure type (ex. kaolinte, montmorillonite, etc) and the above layer-structure type. Layer-structure inorganic clay minerals take water molecules into a unit space between the layers, and then swelled. By utilizing this property, the hydrogen peroxide in the bleaching agents is to be held as adhered onto the surfaces of the teeth. In the present invention, the layer-structure inorganic clay minerals, which swell in the presence of water, are preferable to use.

Although inorganic clay minerals of fibrous structure type and non-crystal structure type are possible to be swelled by adding water and then mixing with a high speed mixer, the layer-structure clay minerals have a merit because of no such machine required.

The following are examples of inorganic clay minerals, but not limited to: dickite, nacrite, kaolinite, anorthite, halloysite, metahalloysite, chrysotile, lizardite, serpentine, antigorite, beidellite, montmorillonite, sauconite, stevensite, nontronite, saponite, hectorite, vermiculite, smecnite, sepiolite, nacrite, illite, sericite, glauconite-montmorillonite, roselite-montmorillonite, chlorite-vermiculite, illite-montmorillonite, halloysite-montmorillonite, kaolinite-montmorillonite.

Among the above inorganic clay minerals, montmorillonite, sauconite, smecnite, stevensite, beidellite, nontronite, saponite, hectorite, vermiculite, nacrite, and sepiolite are particularly preferable for the present invention. These inorganic clay minerals to use are natural products and synthesized products, and also the mixtures of the two or more the minerals.

Further, these inorganic clay minerals show a good thickening effect and thixotopic property in comparison with other aqueous thickening agents. Therefore, they show a little sagging and also they are very easy to be rinsed out by water in comparison with organic thickening agents.

The thickening agents of phosphoric acids to be used for the present invention are illustrated as follows: orthophosphoric acid, hypophosphoric acid, diphosphoric acid, metaphosphoric acid, and the like. Further, as phosphates, potassium phosphate, sodium phosphate, and the like are illustrated. In particular, tetra-sodium pyrophosphate is preferable.

The tooth bleaching compositions of the present invention are characterized by mixing the three constituents mentioned above and using, thereby being possible to use as a gel type or a paste type having sufficiently high viscosity. The viscosity of the bleaching compositions are, in view point of little sagging from the patient teeth and also keeping reasonable amount of the bleaching constituent on the teeth, preferably a range of 1,000 to 100,000 centipoise, more preferably a range of 5,000 to 50,000 centipoise. The viscosity of the range causes no sagging of the bleaching compositions applied to the tooth surface being the angle of 45 degrees to horizontal level. It is not possible to decide the amount of necessary thickening agents sweepingly since it depends on a variety of the thickening agents being used, however, generally a range of 1 to 5% by weight in the bleaching agents gives sufficient results.

The bleaching compositions of the present invention are to be used as homogeneous sol or paste prepared by combining, kneading and dispersing titanium dioxide, the chemical compound generating hydrogen peroxide in a aqueous solution and the thickening agent into water. The blending methods are not limited to, therefore any compositions obtained by any methods of blending the three constituents above are covered by the present invention. In this case, the preparation means and devices of the bleaching compositions such as combining, kneading, dispersing or so on, and applying the bleaching compounds to teeth are not limited, therefore, it is possible to select and use suitable means, devices and/or the like. Further, according to circumstances, it is possible that two of the three constituents above are combined, kneaded and dispersed in advance, and then the rest is combined, kneaded and dispersed immediately before the use.

The bleaching compositions of the present invention prevent the hydrogen peroxide from its decomposition by holding at storage temperature not exceeding 10° C. The storage temperature of the bleaching compositions is preferably not exceeding 10° C., more preferably not exceeding 5° C. In the viewpoint of handling, it is not preferable to hold them below the freezing temperatures that causes to frozen. Further, it is preferable to store them with a shield from the light.

A method of applying the bleaching compositions on tooth surfaces is illustrated as suitable that the bleaching compositions are applied directly to the surfaces. The bleaching of discolored teeth is proceeded that the bleaching composition is applied to the tooth surfaces and then the applied area is irradiated by light once, preferably repeated plural times. The light to be used is to contain a suitable wavelength absorbed by titanium dioxide, then initiating photocatalytic action and also preferably has rarely adverse affect to human body. Such a wavelength is a light contained wavelength of 300 nm or longer, preferably 350 nm or longer, more preferably 400 nm or longer. The light source examples to be used for the light of the present invention are the following: An incandescent lamp, a fluorescent lamp, a halogen light bulb, a black light, a metalhalide lamp, a xenon lamp, a mercury lamp, a UV lamp, a LED (Light Emitting Diode) lamp, a semiconductor laser, and the like. The light of these light sources from which unnecessary wavelengths are cut out by using a proper filter is guided and irradiated to the tooth surfaces on which the bleaching composition is applied. These applications and irradiation are repeated optionally corresponding to the intensity of the tooth discoloration. In case of applying operation such as applying the bleaching composition to the tooth surfaces, it would be done that the new composition is applied every about 15 to 20 minutes and the interval and frequency are properly decided corresponding to the condition of the teeth. The bleaching compositions of the present invention are effective to bleach a vital tooth as well as a non-vital tooth and show remarkable effects so as to bleach it safely and simply.

The main action of the bleaching compositions of the present invention is the bleaching action initiated by multiplicative effects of the titanium dioxide photocatalyst, low concentration of hydrogen peroxide and the thickening agent. That is, titanium oxide generates electrons and positive holes by the light irradiation, then it initiates a chemical reaction with hydrogen peroxide to generate active oxygen. The active oxygen shows significantly stronger oxidative force compared with ozone, therefore, it is able to decompose almost all of organic compounds to carbon dioxide. Further, the bleaching composition applied to tooth surfaces is kept without sagging and enough amounts for bleaching the discolored teeth can be supplied, accordingly the handling as well as the safety is much improved.

The present invention relates to the bleaching compositions bleaching discolored teeth by applying these on the tooth surfaces and then bleaching it based on the photocatalytic action initiated by light irradiation to the applied area. The bleaching composition is characterized by combining titanium dioxide initiating the photocatalyst action with the light irradiation, the chemical compound generating hydrogen peroxide in a aqueous solution and the thickening agent. The following results are shown, therefore the contribution to esthetic improvement of the teeth by the present invention is significant:

(1) Considerable improvements of bleaching treatment due to easy application of the bleaching composition on the tooth surfaces, (2) It is highly safe due to controlled scattering and/or attaching to the mucous membrane of the solution, and also due to the remarkable bleaching effects through the solution of the low hydrogen peroxide concentration, (3) Greatly shortened the bleaching time, (4) Remarkable bleaching results, and the like.

The present invention is explained by the following examples, however, the present invention is not limited by the examples.

EXAMPLES 1 to 14 AND COMPARABLE EXAMPLE (1) Preparation of the Bleaching Compositions Titanium dioxide, a thickening agent, a chemical compound generating hydrogen peroxide in an aqueous solution and distilled water are mixed so as to obtain the bleaching compositions, which are composed of the constituents shown in Table 1, wherein the concentration of the hydrogen peroxide in the bleaching compositions measured by the permanganate titration.

(2) Bleaching the Discolored Tooth By using the bleaching compositions obtained above (1), bleaching treatments have done followed the process below:

1) As preliminary arrangements, the plaque, the tartar, the tar and the like are removed from the discolored tooth surface by a using ultrasonic waves scaler.

2) The tooth surface was cleaned-by using rubber-cup and etc., and a conventional method and dried.

3) A plain moisture-proofing method is carried out.

4) A bleaching composition prepared above (1) was applied on the tooth surface and followed by irradiation of ultraviolet rays having the wavelength of 350 nm and over.

5) An irradiation time is 5 minutes and the application of the new bleaching composition and irradiation are repeated every time.

The results are shown in Table 2, wherein the discoloration intensities of the used teeth (extracted) are classified as follows;

F1: entire crown uniformly colored light yellow, brown and gray with no striations.

F2: entire crown uniformly colored a deeper shade than F1, with no striations.

F3: deep gray and bluish gray with striations.

F4: entire crown discolored to extremely deep purple and grayish purple

TABLE 1

| | | Titanium Dioxide | | | Thickening Agent | | Oxidative Chemical | |
| --- | --- | --- | --- | --- | --- | --- | --- | --- |
| | Trade Name | Crystal type | Particle Diameter (nm) | Content (wt %) | Type | Content (wt %) | Type | Content (wt %) |
| Example 1 | TAYCA AMT-100 | Anatase | 6 | 0.060 | Hectorite | 1.8 | $H_2O_2$ | 5.8 |
| Example 2 | TAYCA JA-1 | Anatase | 180 | 0.048 | Hectorite | 1.8 | $H_2O_2$ | 5.8 |
| Example 3 | TAYCA JA-1 | Anatase | 180 | 0.060 | Hectorite | 1.8 | Sodium perborate | 5.8 |
| Example 4 | TAYCA JA-1 | Anatase | 180 | 0.069 | Hectorite | 1.8 | Sodium perborate | 5.8 |
| Example 5 | Ishihara Techno TTO-55 | Rutile | 35 | 0.060 | Hectorite | 1.8 | $H_2O_2$ | 5.8 |
| Example 6 | TAYCA TKS-201 | Anatase | 5 | 0.060 | Hectorite | 1.8 | $H_2O_2$ | 5.8 |
| Example 7 | TAYCA MT-150A | Rutile | 15 | 0.060 | Hectorite | 1.8 | $H_2O_2$ | 5.8 |
| Example 8 | TAYCA MT-150A | Rutile | 15 | 0.030 | Hectorite | 2.2 | $H_2O_2$ | 3.2 |

TABLE 1-continued

| | Titanium Dioxide | | | | Thickening Agent | | Oxidative Chemical | |
|---|---|---|---|---|---|---|---|---|
| | Trade Name | Crystal type | Particle Diameter (nm) | Content (wt %) | Type | Content (wt %) | Type | Content (wt %) |
| Example 9 | TAYCA AMT-600 | Anatase | 35 | 0.100 | Sepiolite | 2.0 | $H_2O_2$ | 5.5 |
| Example 10 | Shouwa Titanium F6 | Anatase | 17 | 0.500 | Montmotillonite | 1.6 | $H_2O_2$ | 7.0 |
| Example 11 | TAYCA AMT-600 | Anatase | 6 | 0.010 | Nacrite | 1.0 | $H_2O_2$ | 10 |
| Example 12 | TAYCA AMT-150A | Rutile | 15 | 0.100 | Saponite | 3.5 | $H_2O_2$ | 15 |
| Example 13 | TAYCA AMT-600 | Anatase | 35 | 0.060 | Phosphoric acid | 1.0 | $H_2O_2$ | 6.0 |
| Example 14 | TAYCA AMT-150A | Rutile | 15 | 0.060 | Tera-sodium pyrophosphate | 1.5 | $H_2O_2$ | 5.8 |
| Comparative Example | TAYCA AMT-100 | Anatase | 6 | 0.060 | — | — | $H_2O_2$ | 5.8 |

TABLE 2

| | The intensity of Initial discoloration | Wavelenght (nm) | Treatment time (min) | The intensity of discoloration after treatment |
|---|---|---|---|---|
| Example 1 | F3.0 | 385 | 30 | F1.5 |
| Example 2 | F3.5 | 385 | 30 | F3.0 |
| Example 3 | F3.5 | 385 | 30 | F2.5 |
| Example 4 | F3.5 | 385 | 30 | F3.0 |
| Example 5 | F3.5 | 385 | 30 | F1.5 |
| Example 6 | F3.5 | 385 | 10 | F1.5 |
| Example 7 | F3.5 | 385 | 10 | F1.5 |
| Example 8 | F3.5 | 300 | 20 | F2.0 |
| Example 9 | F3.5 | 350 | 60 | F2.0 |
| Example 10 | F3.5 | 365 | 60 | F3.0 |
| Example 11 | F3.5 | 400 | 60 | F3.0 |
| Example 12 | F3.5 | 385 | 40 | F3.0 |
| Example 13 | F3.0 | 385 | 15 | F2.0 |
| Example 14 | F3.0 | 385 | 15 | F1.5 |
| Comparative Example | F3.5 | 385 | 120 | F3.0 |

Industrial Applicability

The present invention relates to the method for bleaching discolored teeth by applying a bleaching composition, which comprises the specified constituents having photocatalytic activity, onto the discolored teeth and then irradiating the applied area with light, and also the present invention relates to tooth bleaching compositions useful for the bleaching method.

What is claimed is:

1. A tooth bleaching composition comprising photocatalytic titanium dioxide in an amount of 0.001 to 10% by weight based on the weight of said composition, hydrogen peroxide or a chemical compound capable of generating hydrogen peroxide in an aqueous solution, and a thickening agent in an amount of 1 to 5% by weight based on the weight of said composition, the composition having a viscosity in a range of 1,000 to 100,000 centipoise, and wherein the thickening agent is a layer-structure clay mineral.

2. The tooth bleaching composition according to claim 1, wherein the titanium dioxide is anatase, rutile or brookite.

3. The tooth bleaching composition according to claim 1, wherein the chemical compound capable of generating hydrogen peroxide in an aqueous solution is selected from the group consisting of, perborate, percarbonate, persulfate, perphosphate, calcium peroxide, magnesium peroxide and urea peroxide.

4. The tooth bleaching composition according to claim 1, which includes hydrogen peroxide.

5. The tooth bleaching composition according to claim 1, wherein the content of the chemical compound capable of generating hydrogen peroxide in an aqueous solution is 35% by weight or less, based on the weight of said composition.

6. A method for bleaching a discolored tooth comprising applying the tooth bleaching composition according to claim 1 onto the surface of a discolored tooth and irradiating the applied surface with light.

7. The method according to claim 6, wherein the wavelength of the irradiating light is 300 nm or longer.

8. The tooth bleaching composition according to claim 2, wherein the chemical compound capable of generating hydrogen peroxide in an aqueous solution is selected from the group consisting of perborate, percarbonate, persulfate, perphosphate, calcium peroxide, magnesium peroxide and urea peroxide.

9. The tooth bleaching composition according to claim 8, which includes hydrogen peroxide.

10. The tooth bleaching composition according to claim 1, which further includes water.

11. The tooth bleaching composition according to claim 10, which includes hydrogen peroxide.

12. A tooth bleaching composition comprising photocatalytic titanium dioxide in an amount of 0.001 to 10% by weight based on the weight of said composition, hydrogen peroxide or a chemical compound capable of generating hydrogen peroxide in an aqueous solution, and a thickening agent in an amount of 1 to 5% by weight based on the weight of said composition, the composition having a viscosity in a range of 1.000 to 100,000 centipoise, and wherein said thickening agent is hectorite.

13. A method for bleaching a discolored tooth comprising applying the bleaching composifion according to claim 12 onto the surface of a discolored tooth and irradiating the applied surface area with light.

14. The tooth bleaching composition according to claim 12, wherein hydrogen peroxide is included in the composition in an amount of 10% by weight or less.

15. The tooth bleaching composition according to claim 1, wherein the titanium dioxide is particulate titanium dioxide coated with calcium phosphate.

16. The tooth bleaching composition according to claim 1, wherein the titanium dioxide is in particulate form, having a particle diameter of 1 to 500 nm.

17. The tooth bleaching composition according to claim 1, wherein the amount of titanium dioxide in the composition is in a range of 0.01 to 1% by weight.

18. The tooth bleaching composition according to claim 1, wherein the amount of titanium dioxide in the composition is in a range of 0.01 to 0.1% by weight.

19. The tooth bleaching composition according to claim 1, wherein the viscosity of the composition is in a range of 5,000 to 50,000 centipoise.

* * * * *